(12) United States Patent
Murphy et al.

(10) Patent No.: US 7,306,938 B2
(45) Date of Patent: Dec. 11, 2007

(54) HIGH THROUGHPUT SCREEN FOR INHIBITORS OF FATTY ACID BIOSYNTHESIS IN BACTERIA

(75) Inventors: Christopher Murphy, Upton, MA (US); Philip Youngman, Boston, MA (US)

(73) Assignee: Millennium Pharmaceuticals, Inc., Cambridge, MA (US)

(*) Notice: Subject to any disclaimer, the term of this patent is extended or adjusted under 35 U.S.C. 154(b) by 605 days.

(21) Appl. No.: 10/683,482

(22) Filed: Oct. 10, 2003

(65) Prior Publication Data

US 2005/0239157 A1    Oct. 27, 2005

Related U.S. Application Data (62) Division of application No. 09/474,140, filed on Dec. 29, 1999, now Pat. No. 6,656,703.

(51) Int. Cl.
*C12N 1/20* (2006.01)
*C12Q 1/18* (2006.01)
*C12Q 1/68* (2006.01)
*G01N 33/567* (2006.01)

(52) U.S. Cl. .................... 435/252.3; 435/32; 435/6; 435/7.2; 435/69.2

(58) Field of Classification Search ............ None
See application file for complete search history.

(56) References Cited

U.S. PATENT DOCUMENTS

| | | | |
|---|---|---|---|
| 5,614,551 A * | 3/1997 | Dick et al. ............ 514/454 |
| 5,759,837 A * | 6/1998 | Kuhajda et al. ....... 435/193 |
| 6,153,381 A | 11/2000 | Rothstein et al. | |
| 6,284,487 B1 | 9/2001 | Stahl et al. | |
| 6,316,244 B1 * | 11/2001 | Freestone et al. ....... 435/252.1 |
| 6,348,321 B1 | 2/2002 | Stahl et al. | |
| 6,559,176 B1 * | 5/2003 | Bassler et al. ............ 514/408 |
| 6,656,703 B1 * | 12/2003 | Murphy et al. .......... 435/32 |
| 2002/0037495 A1 * | 3/2002 | Gutierrez et al. ........ 435/4 |
| 2002/0132814 A1 * | 9/2002 | Oethinger et al. ..... 514/253.08 |

(Continued)

FOREIGN PATENT DOCUMENTS

WO      98/57618    * 12/1998

(Continued)

OTHER PUBLICATIONS

Subrahmanyam, S et al (Sep. 1998) Journal of Biochemistry, pp. 4596-4602, vol. 180(17) Overproduction of a functional fatty acid biosynthetic enzyme blocks fatty acid synthesis in *Escherichia coli*.*

(Continued)

*Primary Examiner*—Mark Navarro
*Assistant Examiner*—Ginny Allen Portner
(74) *Attorney, Agent, or Firm*—Fish & Richardson P.C.

(57) ABSTRACT

Methods for identifying compounds that are inhibitors of bacterial fatty acid biosynthesis are disclosed. Such compounds can be used as lead compounds in methods for preparing antibacterial agents for treating bacterial infections (e.g., in humans, animals, and plants). Inhibitors of bacterial fatty acid synthesis can also be tested for their ability to inhibit synthesis of acylated homoserine lactones. Compounds that inhibit synthesis of acylated homoserine lactones can be used as inhibitors of bacterial virulence. The disclosed methods allow for high throughput screening of libraries of test compounds.

18 Claims, 6 Drawing Sheets

U.S. PATENT DOCUMENTS

| | | | |
|---|---|---|---|
| 2004/0024050 A1* | 2/2004 | Smith et al. | 514/449 |
| 2004/0024068 A1* | 2/2004 | Levy et al. | 514/575 |
| 2006/0063721 A1* | 3/2006 | Miller et al. | 514/23 |
| 2006/0229259 A1* | 10/2006 | Miller et al. | 514/23 |

FOREIGN PATENT DOCUMENTS

| | | | |
|---|---|---|---|
| WO | 99/27786 | * | 6/1999 |

OTHER PUBLICATIONS

Givskov, M et al, Journal of Bacteriology, Nov. 1996, vol. 178(22), pp. 6618-6622.*

Bassler, Bonnie L , Current Opinion in Microbiology, 1999, vol. 2, pp. 582-587.*

Whiteley, M et al, PNAS, Nov. 23, 1999, vol. 96, No. 24, pp. 13904-13909.* de Boer et al. , "Molecular genetic analysis of enoyl-acyl carrier protein reductase inhibition by diazaborine", *Molecular Microbiology*, vol. 31 (2), pp. 443-450 (1999).

Foulger et al., "A 28 kbp segment from the spoVM region of the *Bacillus subtilis* 168 genome," *Microbiology*, 144, pp. 801-805 (1998).

Heath et al., "Broad spectrum Antimicrobial Biocides Target the FabI Component of Fatty Acit Synthesis", *Journal of Biological Chemistry*, vol. 273, No. 46, pp. 30316-30320 (1998).

Heath et al., "Mechanism of Triclosan Inhibition of Bacterial Fatty Acid Synthesis", *Journal of Biological Chemistry*, vol. 274, No. 16, pp. 11110-11114 (1999).

Hoang et al., "Characterization of *Pseudomona aerugionosa* Enoyl-Acyl Carrier Protein Reductase (FabI): a Target for the Antimicrobial Triclosan and Its Role in Acylated Homoserine Lactone Synthesis", *Journal of Bacteriology*, vol. 181, No. 17, pp. 5489-5497 (1999).

Hourdou et al., "Specific Inhibition Of Iturin Biosynthesis By Cerulenin" *Canadian Journal Of Microbiology* 36(3):164-168, 1990.

Jackowski et al., "Acetoacetyl-acyl Carrier Protein Synthase", *Journal of Biological Chemistry*, vol. 264, No. 13, pp. 7624-7629 (1989).

Kunst et al., "The complete genome sequence of the Gram-positive bacterium *Bacillus subtilis*," *Nature*, vol. 390, 249-256, Nov. 1997.

Levy et al., "Molecular basis of triclosan activity", *Nature*, vol. 398, pp. 383-384 (1999).

Magnuson et al., "Regulation of Fatty Acid Biosynthesis in *Escherichia coli*", *Microbiological Reviews*, vol. 57, No. 3, pp. 522-542 (1993).

McMurry et al., "Triclosan targets lipid synthesis" *Nature*, vol. 394, pp. 531-532 (1998).

Moche et al., "Structure of the Complex between the Antibiotic Cerulenin and Its Target, β-Ketoacyl-Acyl Carrier Protein Synthase", *Journal of Biological Chemistry*, vol. 274, No. 10, pp. 6031-6034 (1999).

Morbidoni et al., "*Bacillus subtilis* Acyl Carrier Protein Is Encoded in a Cluster of Lipid Biosynthesis Genes", *Journal of Bacteriology*, vol. 178, No. 16, pp. 4794-4800 (1996).

Noback et al., "The 172 kb prk A-add-AB region from 83 to 97 of the *Bacillus subtilis* chromosome contains several dysfunctional genes, the glyB marker, many genes encoding transporter proteins, and the ubiquitous hit gene," *Microbiology*, 144 pp. 859-875 (1998).

Omura, "Cerulenin", *Methods in Enzymology*, vol. 72, pp. 521-532 (1981).

Quémard et al., "Enzymatic Characterization of the Target for Isoniazid in Mycobacterium", *Biochemistry*, vol. 34, No. 26, pp. 8235-8241 (1995).

Schujman et al., "De novo fatty acid synthesis is required for establishment of cell type-specific gene transcription during sporulation in *Bacilius subtilis*," *Molecular Microbiology*, 29 (5), pp. 1215-1224, 1998.

Val et al., "In Vivo Evidence that S-Adenosylmethionine and Fatty Acid Synthesis Intermediates Are the Substrates for the LuxI Family of Autoinducer Synthases." *Journal of Bacteriology*, vol. 180, No. 10, pp. 2644-2651, 1998.

Attachment 1: Sequence Match to SEQ ID #1. US-09-474-140-1. rge; Mon., May 21, 2001.

Attachment 2: Sequence Match to SEQ ID #3. US-09-474-140-3. rge; Mon., May 21, 2001.

Attachment 3: *Bacillus subtilis* promoters and genes. Accession No. 1997:748948 Caplus.

Levy et al., "Molecular basis of triclosan activity", *Nature*, vol. 398, pp.383-384 (1999).

Magnuson et al., "Regulation of Fatty Acid Biosynthesis in *Escherichia coli*", *Microbiological Reviews*, vol. 57, No. 3, pp. 552-542 (1993).

McMurry et al., "Triclosan targets lipid synthesis" *Nature*, vol. 394, pp. 531-532 (1998).

Moche et al., "Structure of the Complex between the Antibiotic Cerulenin and Its Target, β-Ketoacyl-Acyl Carrier Protein Synthase", *Journal of Biological Chemistry*, vol. 274, No. 10, pp. 6031-6034 (1999).

Morbidoni et al., "*Bacillus subtilis* Acyl Carrier Protein Is Encoded in a Cluster of Lipid Biosynthesis Genes", *Journal of Bacteriology*, vol. 178, No. 16, pp. 4794-4800 (1996).

Noback et al., "The 172 kb prk A-add-AB region from 83 to 97 of the *Bacillus subtilis* chromosome contains several dysfunctional genes, the glyB marker, many genes encoding transporter proteins, and the ubiquitous hit gene," *Microbiology*, 144 pp. 859-875 (1998).

Omura, "Cerulenin", *Methods in Enzymology*, vol. 72, pp. 521-532 (1981).

Quémard et al., "Enzymatic Characterization of the Target for Isoniazid in Mycobacterium", *Biochemistry*, vol. 34, No. 26, pp. 8235-8241 (1995).

Schujman et al., "De novo fatty acid synthesis is required for establishment of cell type-specific gene transcription during sporulation in *Bacilius subtilis*," *Molecular Microbiology*, 29 (5), pp. 1215-1224, 1998.

Val et al., "In Vivo Evidence that S-Adenosylmethionine and Fatty Acid Synthesis Intermediates Are the Substrates for the LuxI Family of Autoinducer Synthases." *Journal of Bacteriology*, vol. 180, No. 10, pp. 2644-2651, 1998.

Attachment1: Sequence Match to SEQ ID #1. US-09-474-140-1. rge; Mon., May 21, 2001.

Attachmennt 2: Sequence Match to SEQ ID #3. US-09-474-140-3. rge; Mon., May 21, 2001.

Attachment 3: *Bacillus subtilis* promoters and genes. Accession No.: 1997:748948 Caplus.

* cited by examiner

FIG. 1

PyhfB Promoter Sequence (SEQ ID NO: 1)
TTTCTTTTTCATAGATTCCTATCTACActtctcttttttgtaaaaacc
ttcttttagtaccagatactaatatctagtgttataatctgaccataagg
agtgattcatatgtcaaaagcaaaaattacagctatcggcacctatgcgcc
gagcagacgtttaaccaatgcagatttagaaaagatcgttgatacctctga
tgaatggatcgttcagcgcacaggaatgagagaacgccggattgcggatga
acatcaatttacctctgatttatgcatagaagcggtgaagaatctcaagaG
CCGTTATAAAGGAACGCTT

FIG. 2

PyjaXY Promoter Sequence (SEQ ID NO: 2)
CACATCCAACTGCATACGCCtcctttccatataccatactctatgagtaag
atgaactgatagtttagacgaatatattgccatgtgaaaaaaataggata
gaattagtacctgatactaataattgatcacaacctgattgatcttctaaa
tttaagatataaaggagtcttccctaatgaaagctggaatacttggtgttg
gacgttacattcctgagaaggttttaacaaatcatgatcttgaaaaaatgg
ttgaaacttctgacgagtggattcgtacaagaacaggaatagaagaaagaa
gaatcgcagcagatgatgtgttttcatcacatatggctgttgcagcagcga
aaaatgcgctggaacaagctgaagtggctgctgaggatctggatatgatct
tggttgcaactgttacacctgatcagtcattccctacggtctcttgtatga
ttcaagaacaactcggcgcgaagaaagcgtgtgctatggatatcagcgcgg
cttgtgcgggcttcatgtacggggttgtaacCGGTAAACAATTTATTGAAT

FIG. 3

PylpC Promoter Sequence (SEQ ID NO: 3)
TGTGTTAAGAGATGAATTGCtgaagagcggagtaatggacggggaaaaatt
aagctgagtatcagaagttttggtgttcagccagaaacaatcgttgcatt
ccaatctatgaaattatatactactattagtacctagtcttaattgtccgg
atggtgtttagatatgagaagaaataagagagaacgccaggaattacttca
gcagacgattcaagcaacccctttattacagatgaagaactagcgggtaa
attcggggtgagcatccagacgatacgtttggaccgcttagagctttccat
acctgaactgagagaaagaattaagaacgtggcagagaaaacacttgagga
cgaagtgaagtCCCTGTCACTTGATGAAGTT

FIG. 4

PyydK Promoter Sequence (SEQ ID NO: 4)
CTAGTCTCGTATAATCTCTCactttccccgacatttcacccacccttcgt
tttggttacgcttcattataattgtaacggtataatttatcaattccgaa
acaaaatatttacgcactaactatcattgtaagcggtttatgctataattt
tgacaagtgaaactaaacgaataaatgaggaatgcgtatgttaaaatacca
gcaaatcgcaacggaaattgaaacatatatagaagaacaccagcttcagca
gggagacaaactgccagtcctagaaacctcatggcccagtttgaagtcag
caaaagcaccatcacaaagtccctcgagctattagagcaaaaggcgcgat
ctttcaggtcagaggaagcggcattttcgtcagaaacataaacgaaaagg
ctatatcagccttctgtcgaatcagggatttaaaaaagatctCGAGGATTT
CAACGTCACCT

HIGH THROUGHPUT SCREEN FOR INHIBITORS OF FATTY ACID BIOSYNTHESIS IN BACTERIA

CROSS-REFERENCE TO RELATED APPLICATION

This application is a divisional of U.S. patent application Ser. No. 09/474,140 (now U.S. Pat. No. 6,656,703), which was filed on Dec. 29, 1999.

FIELD OF THE INVENTION

The invention relates to methods for identifying inhibitors of fatty acid biosynthesis in bacteria.

BACKGROUND OF THE INVENTION

Fatty acid biosynthesis (FAB) is necessary for the production of bacterial cell walls, and therefore is essential for the survival of bacteria (Magnuson et al., 1993, Microbiol. Rev. 57:522-542). The fatty acid synthase system in *E. coli* is the archetypal type II fatty acid synthase system. Multiple enzymes are involved in fatty acid biosynthesis, and genes encoding the enzymes fabH, fabD, fabG, acpP, and fabF are clustered together on the *E. coli* chromosome. Clusters of FAB genes have also been found in *Bacillus subtilis, Haemophilus influenza* Rd, *Vibrio harveyi*, and *Rhodobacter capsulatus*. Examples of FAB genes in *B. subtilis* include fabD, yjaX, and yhfB (encoding synthase III), fabG, ywpB, yjbW, yjaY, ylpC, fabG, and acpA. The ylpC, fabG, and acpA genes are contained within a single operon that is controlled by the PylpC promoter.

Figure 1:
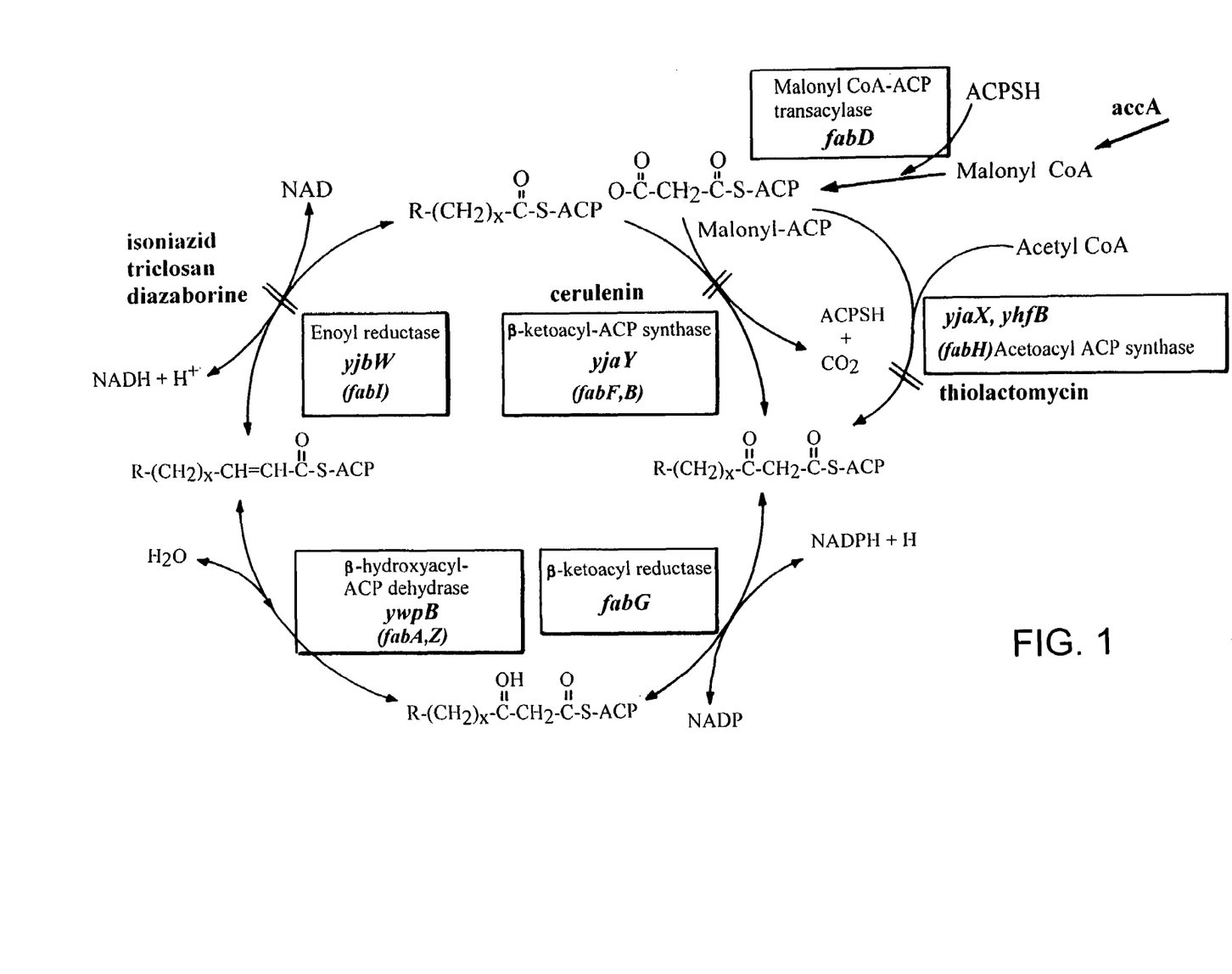
FIG. 1 is a schematic representation of the bacterial fatty acid biosynthesis pathway. The targets of several fatty acid biosynthesis inhibitors are shown.

Using genetic and biochemical methods, the targets and mechanisms of action of several inhibitors of the elongation part of the FAB pathway have been identified (FIG. 1). The FAB inhibitor cerulenin inhibits β-ketoacyl-ACP synthase, and the inhibitor thiolactomycin inhibits acetoacyl ACP synthase (Omura, 1981, Meth. Enzymol. 72:520-532; Moche et al., 1999, J. Biol. Chem. 274:6031-6034; and Jackowski et al., 1989, J. Biol. Chem. 264:7624-7629). The FAB inhibitors isoniazid, triclosan, and diazaborine inhibit enoyl-acyl carrier protein reductase (Quemard et al., 1995, Biochem. 34:8235-8241; McMurray et al., 1998, Nature 394:531-532; Heath et al., 1998, J. Biol. Chem. 273:30316-30320; Heath et al., 1999, J. Biol. Chem. 274:11110-11114; Levy et al., 1999, Nature 398:383-384; and DeBoer et al., 1999, Mol. Microbiol. 31:443-450). In *Pseudomonas aeruginosa*, triclosan has been shown to inhibit the enoyl-acyl carrier protein reductase (FabI), which converts trans-2-enoyl-ACP to acyl-ACP (Hoang and Schweizer, supra). The FAB pathway provides the acyl groups for production of acylated homoserine lactones (HSLs). HSLs are the signaling molecules involved in quorum sensing, i.e., bacterial cell-to-cell signaling, in a wide variety of bacteria. In pathogenic bacteria, such as *Pseudomonas*, quorum sensing is a mechanism for regulating the expression of virulence factors (Hastings and Greenberg, 1999, J. Bacteriol. 181: 2667-2668).

SUMMARY OF THE INVENTION

The invention is based upon the discovery that the activity of promoters of certain genes is increased in the presence of compounds that inhibit *B. subtilis* FAB. Thus, compounds that inhibit FAB can be identified by their ability to increase the activity of the *B. subtilis* PyhfB and PylpC promoters.

Various promoters can be used in the invention, provided that the activity of the promoter is upregulated by a FAB inhibitor, such as cerulenin or triclosan. FAB inhibitors that slow the growth of, or kill, bacteria are candidate antibacterial agents that can be used in methods of treating bacterial infections. The invention thus provides a rapid and convenient method for identifying (i) compounds that inhibit FAB and which can subsequently be derivatized to produce antibacterial agents, as well as (ii) compounds that inhibit FAB and which are antibacterial agents. Because the FAB pathway is involved in the synthesis of HSLs, the invention also provides a method for identifying compounds that inhibit HSL synthesis. Such compounds can be used to inhibit bacterial virulence. If desired, such inhibitors of HSL synthesis can be further derivatized using standard medicinal chemistry techniques to produce inhibitors of virulence having increased potency.

Accordingly, the invention features a method for determining whether a test compound is an inhibitor of bacterial FAB. The method includes: (i) contacting a bacterial cell with a test compound, wherein the bacterial cell contains (a) a promoter (e.g., PyhfB or PylpC), the activity of which is increased in the presence of a compound that inhibits FAB, operably linked to (b) a reporter gene; and (ii) measuring activity of the promoter, wherein an increase in activity, relative to the level of activity of the promoter in the absence of the test compound, indicates that the test compound is an inhibitor of bacterial FAB.

The invention also includes a method for determining whether a test compound is an antibacterial agent, the method comprising: (i) contacting a bacterial cell with a test compound, wherein the bacterial cell contains (a) a promoter (e.g., PyhfB or PylpC), the activity of which is increased in the presence of a compound that inhibits FAB, operably linked to (b) a reporter gene; (ii) measuring activity of the promoter, wherein an increase in activity, relative to the level of activity of the promoter in the absence of the test compound, indicates that the test compound is an inhibitor of FAB; and (iii) determining whether the compound is an antibacterial agent by determining whether the compound kills, or slows the growth of, bacteria. Optionally, the test compound may be further assayed in a biochemical assay (e.g., in an extract of the cell) to determine which step in the pathway is inhibited, and to confirm that the test compound inhibits fatty acid biosynthesis. For example, inhibition of fatty acid biosynthesis can be detected as inhibition of incorporation of acetate into fatty acids or phospholipids. Conventional methods can be used to measure inhibition of incorporation of acetate.

An increase in activity of the promoter can be measured, for example, by measuring expression of a reporter gene that is operably linked to the promoter, such as a lacZ, cat, gus, a green fluorescent protein gene, or a luciferase gene. Other suitable reporter genes are well known in the art and can be used in the invention. If desired, the activity of the promoter can be measured by measuring binding of antibodies to a product of the reporter gene (e.g., a protein encoded by the reporter gene), with an increase in the level of bound antibodies reflecting an increase in activity of the promoter. Alternatively, activity can be measured by measuring the level of mRNA transcribed from the reporter gene, with an increase in the mRNA level reflecting an increase in promoter activity.

The invention also provides methods of preparing (i) an inhibitor of fatty acid biosynthesis and/or (ii) an antibacterial agent. The methods include: screening multiple test compounds by the methods described above; identifying candidate compounds that upregulate promoter activity; isolating one or more lead compounds from the candidate compounds; identifying and selecting a lead compound that inhibits fatty acid biosynthesis or bacterial growth; and formulating the selected lead compound as an inhibitor of fatty acid biosynthesis or as an antibacterial agent. A "lead compound" is a test compound that increases promoter activity by at least 3 times the standard deviation, plus the mean. If desired, lead compounds can subsequently be derivatized using conventional medicinal chemistry methods, as described herein.

Similarly, the invention features methods for preparing (i) an inhibitor of FAB or (ii) an antibacterial agent. The methods include screening multiple test compounds by the methods described above; identifying candidate compounds that upregulate promoter activity; isolating one or more lead compounds from the candidate compounds; derivatizing the lead compound(s), thereby producing a derivative of the lead compound; identifying derivatives that inhibit FAB or bacterial growth; and formulating the derivative as an inhibitor of FAB or as an antibacterial agent (e.g., by admixture with a pharmaceutically acceptable carrier). Inhibitors of FAB and antibacterial agents prepared by such methods also are included within the invention. Such compounds can be used in methods for inhibiting bacterial fatty acid biosynthesis or growth of bacteria in an organism having a bacterial infection.

The invention also provides a method for identifying an inhibitor of bacterial virulence. In such a method, a FAB inhibitor identified by the methods disclosed herein can be further tested for its ability to inhibit the synthesis of HSL. Inhibition of acylated homoserine lactone synthesis can be detected as inhibition of enoyl-acyl carrier protein reductase activity. In a convenient assay, the FAB inhibitor can be tested in vitro for its ability to inhibit the synthesis of N-butyryl-L-homoserine lactone ($C_4$-HSL) in the presence of FabI (enoyl-acyl carrier protein reductase), the HSL synthetase RhlI, the cofactor NADH, and the substrates crotonyl-ACP and S-adenosylmethionine (see, e.g., Hoang and Schweizer, supra). A decreased level of HSL synthesis in the presence of the test compound, relative to the level of HSL synthesis in the absence of the test compound, indicates that the FAB inhibitor is an inhibitor of HSL synthesis. Because HSLs regulate the expression of virulence factors, inhibitors of HSL synthesis can be used to inhibit bacterial virulence, e.g., in a method for treating a bacterial infection. If desired, such HSL synthesis inhibitors can be derivatized, using standard medicinal chemistry techniques as described herein, to produce derivatives that have increased potency as inhibitors of virulence in bacteria.

The invention offers several advantages. For example, various embodiments of the invention can readily be used for high-throughput screening (HTS) of a wide variety of test compounds. Thus, lead compounds can readily be selected from a large number of test compounds. Assays employing the PyhfB and PylpC promoters are capable of detecting FAB inhibitors at concentrations both above and below their minimal inhibitory concentration (MIC). Thus, the assays described herein provide a high level of sensitivity and are expected to detect growth inhibitory (i.e., bacteriocidal) compounds, as well as less potent inhibitors of the FAB pathway, which can be subsequently modified using standard medicinal chemistry techniques and by evaluating structure-activity relationship (SAR) data. Because the assays are cell-based, the assays identify antibacterial agents that can efficiently enter bacterial cells. Thus, the assays allow the identification of potent antibacterial compounds and compounds of structural interest that may have relatively modest potency, but have favorable cell permeability properties. In addition, because FAB is a biochemical pathway, the methods disclosed herein enable the identification of compounds that may inhibit any enzymatic function or step in the pathway.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, technical manuals, and other references mentioned herein are incorporated by reference in their entirety. In case of conflict, the present application, including definitions, will control. In addition, the materials, methods, and examples are illustrative only and not intended to be limiting.

Other features and advantages of the invention will be apparent from the following description of the preferred embodiments thereof, and from the claims.

DETAILED DESCRIPTION

The invention provides a method for determining whether a test compound is an inhibitor of bacterial FAB. The invention derives from the discovery that compounds that inhibit fatty acid biosynthesis cause an increase in the activity of the PyhfB and PylpC promoters. Generally, the method involves determining whether the test compound induces an increase in activity in the PyhfB or PylpC promoter, as indicated by an increase in expression of a reporter gene operably linked to the promoter (i.e., a reporter-based screen). As discussed in detail below, the activity of the PyhfB and PylpC promoters is increased upon inhibition of the FAB pathway. Thus, compounds that increase the activity of the PyhfB or PylpC promoter can be expected to inhibit bacterial fatty acid biosynthesis. Optionally, the test compound can be further tested to confirm that it inhibits fatty acid biosynthesis (i.e., in a biochemical screen). These methods are described in further detail below.

Part I: Reporter-Based Screens

Genetic Constructs: Conventional transcriptional profiling methods can be used to identify promoters that have increased activity in the presence of antibacterial agents such as cerulenin and triclosan, which are inhibitors of FAB. In such an assay, certain bacterial promoters display an increase in activity in the presence of antibacterial agents, as evidenced by an increase in the level of mRNA transcripts of the sequences.

Figure 2:
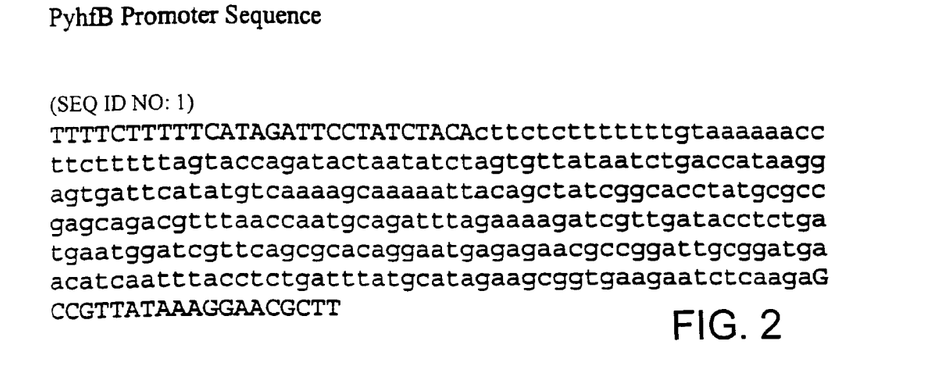
FIG. 2 is a listing of the nucleotide sequence of the PyhfB promoter.
Figure 3:
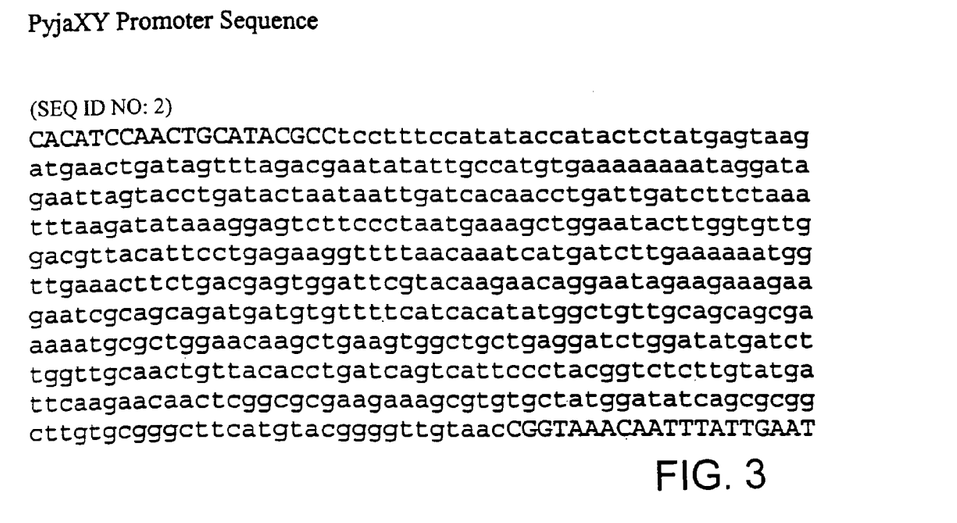
FIG. 3 is a listing of the nucleotide sequence of the PyjaXY promoter.
Figure 4:
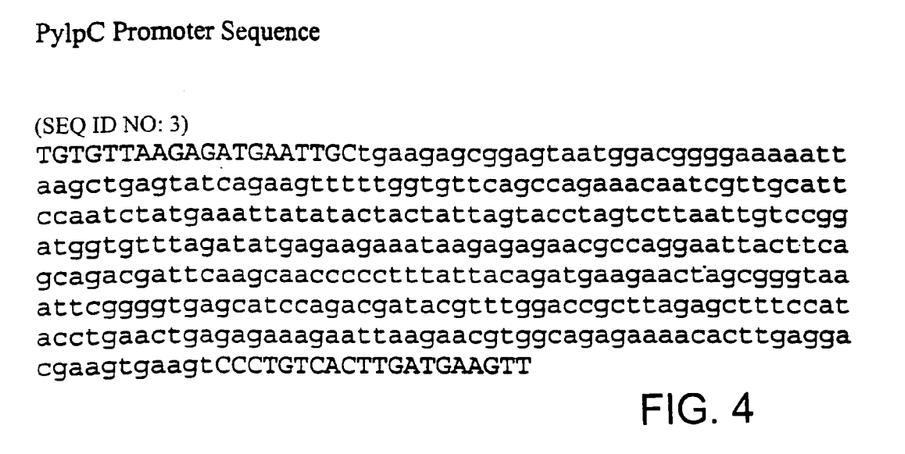
FIG. 4 is a listing of the nucleotide sequence of the PylpC promoter.
Figure 5:
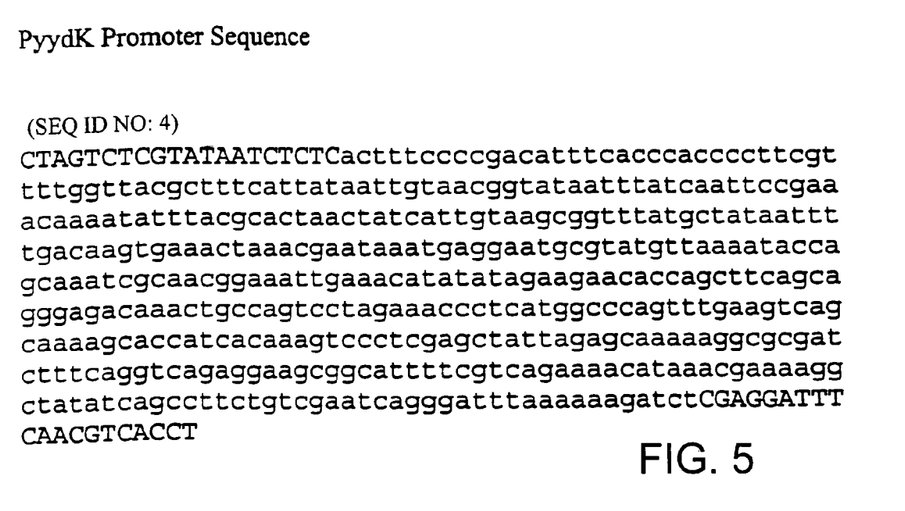
FIG. 5 is a listing of the nucleotide sequence of the PyydK promoter.

A "promoter" is a minimal sequence sufficient to direct transcription; the promoter is located in the 5' region of the native gene. A sequence containing the PyhfB promoter is set forth in FIG. 2 as SEQ ID NO:1. The sequence of the yhfB gene is set forth in GenBank as Accession No. BG13048. A sequence containing the PyjaXY promoter is set forth in FIG. 3 as SEQ ID NO:2. The sequence of the yjaX gene is set forth in GenBank as Accession No. BG13127. A sequence containing the PylpC promoter is set forth in FIG. 4 as SEQ ID NO:3. The sequence of the ylpC gene is set forth in GenBank as Accession No. BG 13400. A sequence containing the PyydK promoter is set forth in FIG. 5 as SEQ ID NO:4. The sequence of the yydK gene is set forth in GenBank as Accession No. BG11484.

To confirm that the activity of a promoter is increased in the presence of an antibacterial agent, each promoter can be operably linked to the coding sequence of a reporter gene, such as the E. coli lacZ gene. The resulting genetic constructs then are inserted into a silent chromosomal location in B. subtilis. Such strains are treated with an antibacterial agent, such as cerulenin or triclosan, and the level of promoter activity, as measured by lacZ expression is measured. An increase in the level of promoter activity, relative to the level of lacZ expression in untreated, control cells, confirms that promoter activity is modulated by the antibacterial agent.

The "reporter gene" can be any sequence the expression of which can be detected or measured, other than the coding sequence to which the promoter naturally is operably linked. Typically, the reporter gene is heterologous to the bacterial strain in which promoter activity is measured. Examples of suitable reporter genes include, without limitation, lacZ, the bacterial chloramphenicol transacetylase (cat) gene, luciferase genes, the bacterial gus gene, and the like. Also included are sequences that encode fluorescent markers, such as green fluorescent protein (GFP). The aforementioned reporter genes, and methods for measuring their expression, are well known in the art.

Bacterial Strains: B. subtilis strains having the PyhfB or PylpC promoter operably linked to the coding sequence of a reporter gene can be used to assay the ability of test compounds to increase activity of the PyhfB or PylpC promoters. If desired, the promoter and reporter gene can be stably integrated into the bacterial chromosome. Examples of such strains include PY79 (amy::PyhfB-lacZ, cat) and PY79 (amy::PylpC-lacZ, cat). Alternatively, the promoter and coding sequence of the reporter gene can be located on a plasmid that is introduced into a bacterium (e.g., E. coli). If desired, a test compound can first be identified as an antibacterial agent by detecting its ability to increase the activity of one of the aforementioned B. subtilis promoters, and then confirming its ability to act as an antibacterial agent by detecting its ability to increase the activity of a second promoter. For example, test compounds can first be screened with the strain PY79 (amy::PyhfB-lacZ, cat). Test compounds that increase the activity of the PyhfB promoter can then be tested for their ability to increase the activity of the PylpC promoter in the strain PY79 (amy::PylpC-lacZ, cat).

Test Compounds: The "test compound" can be any compound, such as a small organic molecule, amino acid, polypeptide, nucleic acid, peptide nucleic acid, carbohydrate, or polysaccharide. The test compound can be synthetic, naturally occurring, or a combination of synthetic and natural components. If desired, the test compound can be a member of a library of test compounds (e.g., a combinatorial chemical library) or a component of a cellular extract or bodily fluid (e.g., urine, blood, tears, sweat, or saliva).

Test compounds that increase the activity of the promoter, relative to the level of promoter activity in the absence of the test compound, are considered inhibitors of bacterial FAB. The level of promoter activity measured in the presence of the test compound then is compared with the level measured in the absence of the test compound. Generally, an increase in the level of promoter activity that is at least 3 times the standard deviation of a test compound set (i.e., a set of one or more test compounds), plus the mean of a test compound set, relative to the level of gene expression in the absence of the test compound, indicates that the test compound is an inhibitor of FAB. Such an increase may be, for, example, 5-fold, 10-fold, 20-fold, 50-fold, or even 100-fold. A relatively high level of induction generally indicates that the test compound has a relatively high level of potency.

Promoter activity, as measured by reporter gene expression, can be measured by any of a number of conventional methods, and the optimal method will depend upon factors such as the nature and function of the reporter gene. In general, suitable assays of reporter gene expression include methods such as (i) assaying the function of a product of the reporter gene (e.g., measuring an enzymatic reaction catalyzed by a product of the reporter gene); (ii) measuring the level of protein expressed from the reporter gene (e.g., by SDS-PAGE or in an immunoassay using antibodies (e.g., polyclonal or monoclonal antibodies) that specifically bind to the product of the reporter gene; and (iii) measuring the level of mRNA transcribed from the reporter gene. Included within the invention are assays that permit high throughput screening of test compounds.

The assays of promoter induction can be carried out in virtually any reaction vessel or receptacle. Examples of suitable receptacles include 96-well plates, 384-well plates, test tubes, centrifuge tubes, and microcentrifuge tubes. The methods can also be carried out on surfaces such as metal, glass, ceramics, paper, polymeric chips, membrane surfaces, resins, or the surface of a matrix-assisted laser-desorption ionization mass spectrometry (MALDI-MS) plate.

Part II: Biochemical Screen

Once a test compound is identified as an inhibitor of FAB using the above-described reporter-based assay, the compound can be further tested, if desired, in a biochemical assay. Such a biochemical assay generally involves measuring inhibition of fatty acid biosynthesis. Various methods for measuring inhibition of fatty acid biosynthesis are known in the art, and can be used in this aspect of the invention (see, e.g., Buttke et al., Biochemistry 17:5282-5286, 1978; Kuhajda et al., PNAS 91:6379-6383, 1994; Weiss et al., Biol. Chem. Hoppe Seyler 367:905-912, 1986; Stoops et al., J. Biol. Chem. 253:4464-4475, 1978; Duronio et al., J. Cell Biol. 113:1313-1330, 1991; Meyer et al., 117:345-350, 1974; Zhao et al., Microbiol. 142:2509-2514, 1996; and Schneiter et al., Mol. Cell. Biol. 16:7161-7172, 1996, which are incorporated herein by reference). Table 1 sets forth various B. subtilis and E. coli fatty acid biosynthesis genes and enzymes, along with the enzymatic reactions that the enzymes catalyze. Standard assays for measuring inhibition of the enzymatic reactions are summarized in Table 1 and can be used in the invention.

If desired, inhibition of fatty acid biosynthesis can be measured in a cell extract that contains all of the components (e.g., enzymes, cofactors, carrier molecules, and buffers) normally necessary for a particular step that is needed in the synthesis of fatty acids. Cell extracts containing enzymes, cofactors, and carrier molecules can be cytoplasmic, cytosolic, or membrane preparations, whole cells, or naturally-occurring or synthetic mixtures composed of natural or unnatural components, or both. Carrier molecules included in the cell extract can include numerous components, such as molecular transport machinery and membranes. The substrate for the reaction can be contained within the cell extract initially, it can be added in solution, e.g., as a dry or liquid additive, or it can be generated in situ (e.g., as the product of another reaction). The substrate can be detectably labeled with a tag, for example, a radiolabel, a fluorescent label, a magnetic label, or as a biotinylated derivative.

chemical modifications can be made according to conventional methods (See, e.g., Wade, Organic Chemistry, Prentice-Hall, Inc., New Jersey, 1987). If structural information of the FAB inhibitor and its target are available, derivatives of the inhibitor can be generated and optimized virtually by using molecular modeling software and conventional methods. Such software is commercially available (e.g., from Tripos Inc., Molecular Simulations, Inc., and MDL Information Systems, Inc).

Use of FAB Inhibitors

A compound identified as a FAB inhibitor or as an antibacterial agent can be used to treat a bacterial infection in an organism (e.g., a plant or mammal, such as a human, dog, cat, cow, etc.). Because fatty acid biosynthesis genes are widely conserved, inhibitors of fatty acid biosynthesis are expected to be useful in inhibiting fatty acid biosynthesis

TABLE 1

Assays of Fatty Acid Biosynthesis Enzymes

| *B. subtilis* Gene and Enzyme | *E. coli* Gene and Enzyme | Reaction Catalyzed by the Enzyme | Assay |
|---|---|---|---|
| fabD malonyl CoA-ACP transacylase | fabD malonyl CoA-ACP transacylase | malonyl-CoA + ACP → malonyl-ACP + CoA | measure incorporation of $^{14}C$ malonate into ACP |
| yjaX and YhfB synthase III | fabH acetoacyl-ACP synthase | malonyl-ACP + acetyl-CoA → acetoacyl-ACP + $CO_2$ | measure incorporation of $^{14}C$ acetyl-CoA into ACP |
| fabG β-ketoacyl-ACP reductase | fabG β-ketoacyl-ACP reductase | acetoacyl-ACP + NADPH → D-hydroxybutyryl-ACP + NADP | measure NADPH oxidation at 340 nm |
| ywpB β-hydroxyacyl-ACP dehydrase | fabA β-hydroxyacyl-ACP dehydrase | β-hydroxybutyryl-ACP ⇌ Crotonyl-ACP + $H_2O$ | in conjunction with fabI, measure NADH oxidation |
| yjbW enoyl reductase | fabI enoyl reductase | crotonyl-ACP + NADH → butyryl-ACP + NAD | measure NAADH oxidation at 340 nm |
| yjaY β-ketoacyl ACP synthase | fabF/B β-ketoacyl ACP synthase | fatty acyl-ACP + malonyl-ACP → β-ketoacyl-ACP + $CO_2$ + ACP | measure β-ketoacyl formation at 303 nm in the presence of $Mg^{2+}$ |

After incubation of the cell extract/substrate mixture under conditions that normally allow the particular step(s) to proceed, the mixture is assayed to determine whether the substrate remains and/or whether the corresponding product or products have been formed. The optimal duration of incubation varies with the particular synthesis step(s) being carried out and also with incubation temperature (e.g., at least 1 hour, 12 hours, 1 day, 2 days, a week, or longer, at, e.g., room temperature or lower, 30° C., 37° C., or higher, depending on the strain of bacteria).

Medicinal Chemistry

Once a compound has been identified as an inhibitor of FAB, principles of standard medicinal chemistry can be used to produce derivatives of the compound. The moieties that are responsible for the compound's activity can be revealed by examining its structure-activity relationships (SAR). Specifically, a person of ordinary skill in the art of chemistry could modify a moiety of the compound to study the effects of the modification on the potency of the compound and thereby produce derivatives of the compound having increased potency (See, e.g., Nagarajan et al., Antibiot. 41:430-438). For example, chemical modifications such as N-acylation, esterification, hydroxylation, alkylation, amination, amidation, oxidation, or reduction can be made. Such in a wide spectrum of bacteria. For example, the compounds can be used to treat infections with gram positive bacteria (e.g., *Bacillus* ssp.), particularly pathogenic bacteria, such as *Streptococcus* ssp. Thus, the compounds can be used, for example, to treat infections caused by *Streptococcus pneumoniae, Streptococcus pyogenes, Streptococcus agalactiae, Streptococcus endocarditis, Streptococcus faecium, Streptococcus sangus, Streptococcus viridans*, or *Streptococcus hemolyticus*. The compounds that are identified as FAB inhibitors or as antibacterial agents using the screening methods of the invention are expected to have activity against a broad spectrum of bacteria.

A composition containing an effective amount of a FAB inhibitor or an antibacterial agent can be administered to an organism in a method of treatment (e.g., topically, orally, nasally, buccally, subcutaneously, or intraperitoneally). Treatment typically includes administering an effective amount of a composition containing a FAB inhibitor or an antibacterial agent to a subject in need of such treatment, thereby inhibiting bacterial growth in the subject. Such a composition typically contains from about 0.1 to 90% by weight (preferably 1 to 20% or 1 to 10%) of the antibacterial agent of the invention in a pharmaceutically acceptable carrier.

Solid formulations of the compositions for oral administration may contain suitable carriers or excipients such gelatin, lactose, acacia, sucrose, kaolin, mannitol, dicalcium phosphate, calcium carbonate, sodium chloride, or alginic acid. Disintegrators that can be used include, without limitation, micro-crystalline cellulose, corn starch, sodium starch glycolate and alginic acid. Tablet binders that may be used include acacia, methylcellulose, sodium carboxymethylcellulose, polyvinylpyrrolidone (Povidone™), hydroxypropyl methylcellulose, sucrose, starch, and ethylcellulose. Lubricants that may be used include magnesium stearates, stearic acid, silicone fluid, talc, waxes, oils, and colloidal silica.

Liquid formulations of the compositions for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents. Various liquid and powder formulations can be prepared by conventional methods for inhalation into the lungs of the mammal to be treated.

Injectable formulations of the compositions may contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, water soluble versions of the compounds may be administered by the drip method, whereby a composition containing the compound and a physiologically acceptable excipient is infused. Physiologically acceptable excipients may include, for example, 5% dextrose, 0.9% saline, Ringer's solution or other suitable excipients. For intramuscular preparations, a sterile formulation of a suitable soluble salt form of the compounds can be dissolved and administered in a pharmaceutical excipient such as Water-for-Injection, 0.9% saline, or 5% glucose solution. A suitable insoluble form of the compound may be prepared and administered as a suspension in an aqueous base or a pharmaceutically acceptable oil base, such as an ester of a long chain fatty acid (e.g., ethyl oleate).

A topical semi-solid ointment formulation typically contains a concentration of the active ingredient from about 0.1 to 20% wt/vol (preferably 0.1 to 2% wt/vol of essentially pure material) in a carrier such as a pharmaceutical cream base. Various formulations for topical use include drops, tinctures, lotions, creams, solutions, and ointments containing the active ingredient and various supports and vehicles.

The optimal percentage of the active ingredient in each composition varies according to the formulation itself and the therapeutic effect desired. Appropriate dosages can readily be determined by those of ordinary skill in the art by monitoring the organism for signs of disease amelioration or inhibition, and increasing or decreasing the dosage and/or frequency of treatment as desired. The optimal amount of the composition used for treatment of conditions caused by or contributed to by bacterial infection may depend upon the manner of administration, the age and the body weight of the subject and the condition of the subject to be treated. Generally, the antibacterial agent is administered to a subject at a dosage of 1 to 100 mg/kg of body weight (preferably at a dosage of 1 to 10 mg/kg of body weight).

Use of Inhibitors of Bacterial Virulence

FAB inhibitors that also are inhibitors of HSL synthesis can be used to inhibit the expression of bacterial virulence factors. As described above for FAB inhibitors generally, inhibitors of bacterial virulence can be administered to an organism in need of treatment. Like other FAB inhibitors identified with the methods of the invention, inhibitors of bacterial virulence can be used to treat infections caused by a broad spectrum of bacteria.

EXAMPLE

The invention is further described by the following example, which is not intended to limit the scope of the invention.

Identification of the PyhfB, PyjaXY, PylpC, and PyydK Promoters

Conventional RNA profiling studies revealed that bacterial cells treated with the FAB pathway inhibitors cerulenin (0.5 µg/ml or 5 µg/ml) and triclosan (0.1 µg/ml or 1 µg/ml) in LB medium at 37° C. for 10, 30, or 60 minute time periods displayed an increase in activity of the PyhfB, PyjaXY, PylpC, and PyydK promoters. Thus, transcriptional profiling indicated that the promoters of these genes were upregulated by antibacterial agents.

*B. subtilis* strains containing a PyhfB, PyjaXY, or PylpC promoter (along with an insignificant portion of the coding sequence) operably linked to the coding sequence of an *E. coli* lacZ reporter gene were used to confirm that the activity of the promoter is upregulated by an inhibitor of fatty acid biosynthesis. Clones containing the PyhfB, PyjaXY, and PylpC promoters have been described in GenBank, and the accession numbers for these clones are set forth in Table 2. The promoters were isolated by PCR amplification of *B. subtilis* genomic DNA using the primers shown in Table 2.

Figure 6:
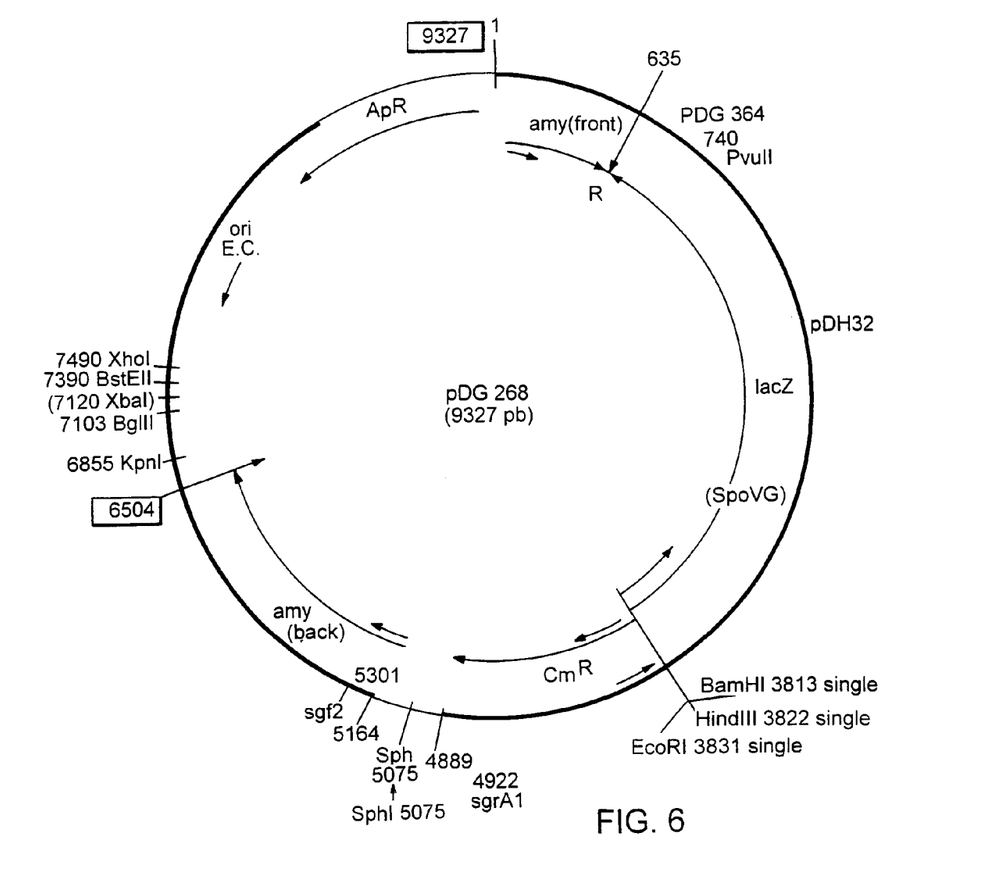
FIG. 6 is a map of the pDG268 vector.

The reporter strains used in these assays were constructed as follows. PCR products containing the promoters were digested with EcoRI and BamHI, and cloned into the multiple cloning site of pDG268, which also had been digested with EcoRI and BamHI. The plasmid pDG268 is a derivative of pGD364 (See, Cutting and Van der Horn, *Molecular Biological Methods for Bacillus*, eds. C. R. Harwood and S. M. Cutting, 1990, John Wiley and Sons, NY, N.Y., pp. 52-54). A schematic representation of pDG268 is set forth in FIG. 6. The plasmid pDG268 is able to replicate in *E. coli*, contains an ampicillin-resistance gene, and encodes a promoter-less lacZ coding sequence. The multiple cloning site (MCS) is positioned such that a promoter of interest can be directionally cloned to drive expression of the lacZ sequence. Adjacent to the MCS, and opposite the lacZ sequence, is a gene encoding chloramphenicol (Cm) resistance for *B. subtilis*. The entire Cm-MCS-lacZ region is flanked by the upstream and downstream section of the *B. subtilis* amyE gene (a "silent" locus in the *B. subtilis* chromosome). Thus, the promoter fusion of interest can be stably integrated by homologous recombination at the amyE site of the *B. subtilis* chromosome by transforming *B. subtilis* cells with the linearized plasmid, and selecting for resistance to chloramphenicol. The promoter fusions were placed at the amyE chromosomal location of the *B. subtilis* strain PY79, which is a wild-type *B. subtilis* strain that is devoid of prophages (Youngman et al., 1984, Mol. Gen. Genet. 195:424-433). The resulting strains were: PY79 (amy::PyhfB::lacZ, cat), PY79(amy::PylpC::lacZ, cat), PY79(amy::PyydK::lacZ, cat), and PY79(amy::PyjaXY::lacZ, cat).

TABLE 2

Primers Used to Isolate Promoters

| Gene | GenBank Accession No. | Upstream Primer | Downstream Primer |
|------|----------------------|-----------------|-------------------|
| yhfB | BG13048 | 5'TTTTCTTTTTCATAGATTCCTATCTACA3' (SEQ ID NO:5) | 5'AAGCGTTCCTTTATAACGGC3' (SEQ ID NO:6) |
| yjaXY | BG13127 | 5'CACATCCAACTGCATACGCC3' (SEQ ID NO:7) | 5'ATTCAATAAATTGTTTACCG3' (SEQ ID NO:8) |
| ylpC | BG13400 | 5'TGTGTTAAGAGATGAATTGC3' (SEQ ID NO:9) | 5'AACTTCATCAAGTGACAGGG3' (SEQ ID NO:10) |
| yydK | BG11484 | 5'CTAGTCTCGTATAATCTCTC3' (SEQ ID NO:11) | 5'AGGTGACGTTCAAATCCTCG3' (SEQ ID NO:12) |

Figure 7:
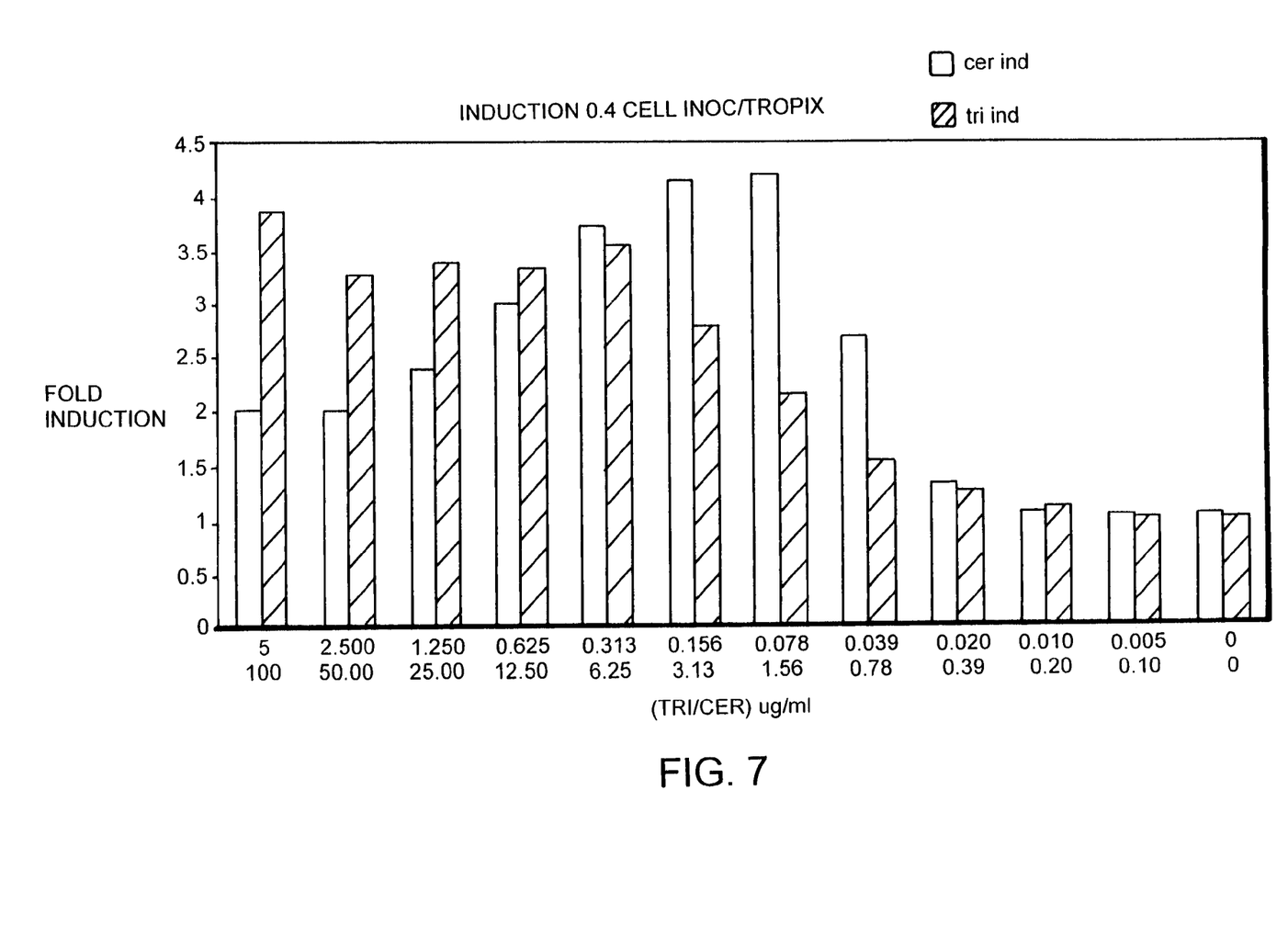
FIG. 7 is a histogram depicting the level of induction of the PyhfB promoter in the presence of varying concentrations of triclosan (tri) and cerulenin (cer).
Figure 8:
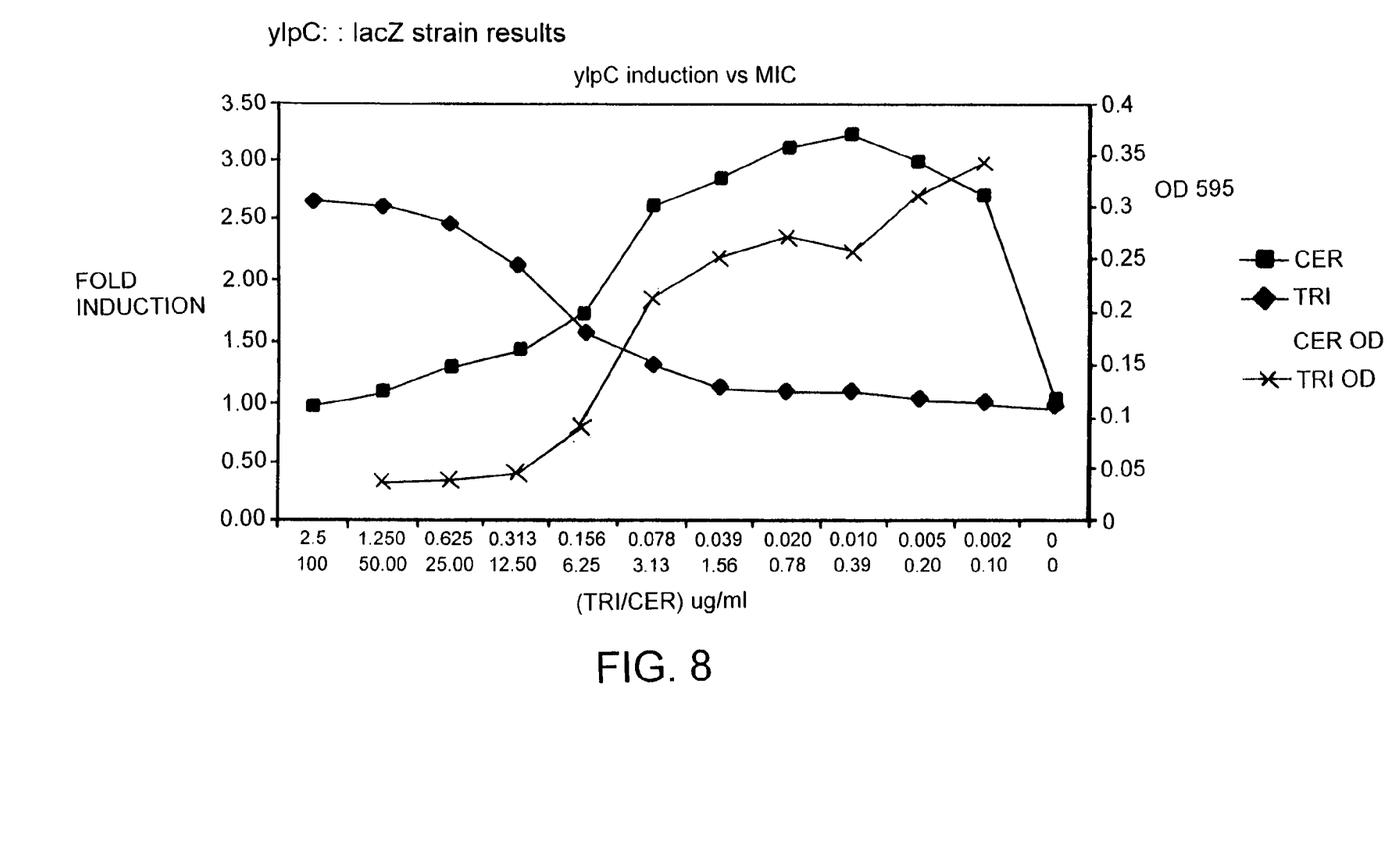
FIG. 8 is a graph depicting the level of induction of the PylpC promoter in the presence of varying concentrations of triclosan (tri) and cerulenin (cer).

The reporter strains were incubated, separately, with triclosan or cerulenin at various concentrations, as shown on the X-axes depicted in FIGS. 7 and 8. Each strain and an antibacterial agent were incubated in a 96-well microplate for 3 hours. β-galactosidase activity was detected using the Tropix Galacton Star™ chemiluminescent substrate (3-chloro-5-(4-methoxyspiro{1,2-dioxetane-3,2'-(4'chloro)-tricyclo-[3.3.1.1$^{3,7}$]decan}-4-yl)phenyl-B-D-galactopyranoside) and the detection method described below. The fold induction of promoter activity was calculated as the level of activity in the samples containing the antibacterial agent divided by the level of activity in the samples that lacked the agent. The results obtained with the strain PY79(amy::PyhfB::lacZ, cat) are represented by FIG. 7, and the results obtained with the strain PY79(amy::PylpC::lacZ, cat) are represented by FIG. 8.

The minimum inhibitory concentrations (MIC) for cerulenin and triclosan were determined for each of the reporter strains. To determine the MIC, a compound of interest (e.g., cerulenin or triclosan) was placed in a 96-well microtiter plate such that the concentration of the compound varies in various wells of the plate (e.g., by using a series of 2-fold dilutions of the compound). Approximately 5,000 cells from a logarithmically-growing culture (e.g., the *B. subtilis* strain PY79) in Luria broth were added to each well (e.g., in a volume of 50-80 μl). The plate then was incubated at 37° C. for approximately 18 hours. The $OD_{600}$ was then read to measure cell growth in each well of the plate. The lowest concentration of the compound that leads to complete killing of the culture (i.e., the concentration of compound for which the $OD_{600}$ nm is equal to a control well that contains only media and the test compound) is deemed the MIC for the particular compound and bacterial strain. The MICs for cerulenin and triclosan were 12.5 μg/ml and 5 μg/ml, respectively, for both of the reporter strains. Such inhibitors can be used as lead compounds, which can subsequently be derivatized using standard medicinal chemistry techniques to produce antibacterial agents. The PY79(amy::PyjaXY::lacZ, cat) strain did not provide significant induction of promoter activity.

Assay for Inhibitors of FAB

Having determined that antibacterial agents such as cerulenin and triclosan increase the activity of the PyhfB and PylpC promoters, bacterial strains containing one or more of these promoters each operably linked to a reporter gene (e.g., lacZ) can be used in a method for determining whether a test compound is an inhibitor of FAB. The following example of such a method describes use of the PyhfB promoter in an initial assay and use of the PylpC promoter in an optional confirmation assay. Comparable reagents, apparatuses, and methods can readily be substituted for those described herein.

Bacterial Strains: The bacterial strain PY79 (amy::PyhfB::lacZ, cat), which contains the PyhfB promoter operably linked to the coding sequence of a lacZ reporter gene, was used in the initial screen for inhibitors of FAB. To prepare a bacterial glycerol stock, the cell culture was mixed at a 1:1 ratio with sterile 50% glycerol, and 1.0 ml aliquots of the suspension were stored in cryovials at −80° C.

To prepare cells for use in the assay of test compounds, 5 μl of the glycerol stock was diluted in 80 ml of low salt LB medium (LB broth containing 5 g/L of NaCl). A 15 μl aliquot of this diluted glycerol stock was then added to 900 ml of low salt LB medium and grown to an $OD_{600}$ of 0.6 in a shaking incubator at 30° C. Generally, a culture having an $OD_{600}$ of 0.4 to 0.6 is suitable for use in the screening assays.

Screening Plates: In this example, chemical libraries containing test compounds at 10 mg/ml in DMSO are diluted to 100 μg/ml with 50 mM HEPES buffer (pH 7.4). The test compounds (e.g., 0.1 μg or 0.05 μg) are dispensed into each well of a microplate (e.g., a 96- or 384-well microplate). The dispensed compounds are dried onto the plates (e.g., by leaving the plates in a fume hood overnight), and the plates are stored in the freezer and then brought to room temperature before being used in the screening assay.

A 50 μl sample of the bacteria is added to each well of the microplate. Cerulenin is used as a control in wells of the microplate that lack a test compound. A stock solution of cerulenin (2,3-Epoxy-4-oxo-7,1-dodecadienamide) is prepared to a concentration of 10 mg/ml in DMSO and stored at −20° C. A working solution of cerulenin is prepared by diluting the cerulenin stock solution to 50 μg/ml with 50 mM HEPES (pH 7.4). A 5 μl aliquot of the 50 μg/ml of cerulenin working solution is added to the plate to provide a control. The bacteria and test compounds (or cerulenin control) are then incubated at 30° C. for approximately 5 hours. If desired, the length and/or temperature of incubation can be increased or decreased. After incubating the cells and test compounds, the plates can be stored at −80° C. if they are not going to be analyzed immediately. Before analysis, the plates should be returned to room temperature, e.g., by leaving the plates in a single layer for one hour at room temperature.

Assay for Induction of Promoter Activity: To assay for an increase in the activity of the PyhfB promoter, an increase in expression of the lacZ reporter gene expression (or expression of an alternative reporter gene) is measured. A 50 μl aliquot of 2× substrate buffer is added to each well of the plate. To produce a 10 ml sample of 2× substrate buffer, the following components are mixed and kept at room temperature: 0.4 ml of Galacton-Star™ substrate (3-chloro-5-(4-methoxyspiro{1,2-dioxetane-3,2'-(4'chloro)-tricyclo-[3.3.1.1$^{3,7}$]decan}-4-yl)phenyl-B-D-galactopyranoside; Tropix, Inc., Cat.# GS100); 2.0 ml of Sapphire II™ luminescence signal enhancer (Tropix, Inc., Cat.#LAX250); and 7.6 ml of lysis buffer (0.026% Na Deoxycholic acid, 0.053% CTAB, 265 mM NaCl, 395 mM HEPES, pH 7.5). The 2× substrate buffer is stable for approximately 2 hours. The plates are incubated at room temperature for 120 minutes before measuring β-galactosidase activity.

A chemiluminescent signal is produced by reaction of β-galactosidase with the Galacton-Star™ substrate (3-chloro-5-(4-methoxyspiro{1,2-dioxetane-3,2'-(4'chloro)-tricyclo-[3.3.1.1$^{3,7}$]decan}-4-yl)phenyl-B-D-galactopyranoside). Chemiluminescence is measured using a TopCount™ microplate reader set as follows: data mode=seconds per count; count time=0.1 minute; count delay=0.10 minute; background subtract=none; half-life correction=no; sample screening=no; and quench indicator=tSIS. Generally, chemiluminescence should be measured before significant signal decay occurs. The read window for the substrate, during which time the plates should be analyzed, is approximately 120 minutes to 180 minutes after initiating the reaction.

The mean and standard deviation of the results obtained for the reactions on a particular plate are measured (excepting the cerulenin control wells). A chemiluminescent signal that is at least 3 times the standard deviation, plus the mean, indicates that the test compound is a "lead" compound, i.e., a compound that increases the activity of the promoter and is a FAB inhibitor. The cerulenin controls described above should produce a chemiluminescent signal that is at least equal to 4 times the mean. The general quality of the analysis of the plate can be determined using Spotfire Pro version 4.0 data analysis software (Spotfire, Inc.; Cambridge, Mass.) by assessing parameters such as the overall hit rate, the random nature of the position of hits, and signal strength consistency over all plates and analyses. Compounds that inhibit FAB may or may not be bacteriocidal or bacteriostatic. Nevertheless, such compounds can be used in the development of antibacterial drugs through the use of standard medicinal chemistry techniques. Thus, the invention includes methods for preparing an antibacterial agent by: screening multiple test compounds as described herein to identify candidate compounds that upregulate promoter activity and therefore are FAB inhibitors; isolating one or more lead compounds from the candidate compounds; determining whether the compound inhibits the growth of a bacterium, in which case the compound can be formulated as an antibacterial agent; and, optionally, derivatizing the lead compound(s) through medicinal chemistry to produce a derivative(s) that inhibits the growth of a bacterium; and formulating the derivative as an antibacterial agent. Optionally, the compound can be characterized in a biochemical assay to determine which step it inhibits in the FAB pathway and/or confirm that the protein is a FAB inhibitor.

Confirmatory Assay: Test compounds that cause an induction of promoter activity of at least 3 times the standard deviation, plus the mean, can be further tested (e.g., at 10 μg/ml and 50 μg/ml) in an optional, "confirmatory" assay. This assay is carried out identically to the above-described assay, except that a bacterial strain containing an alternate promoter operably linked to a reporter gene is used. For example, if the strain PY79(amy::PyhfB-lacZ, cat) is used in the initial screening assay, the strain PY79(amy::PylpC-lacZ, cat) can be used in the confirmatory assay. Other combinations of promoters also can be used in the initial and confirmatory assays. Of course, the test compounds can be re-tested with the strain used in the initial screen. Because the test compounds used in such a confirmatory assay can be expected to result in a high overall level of induction, the wells in four columns of the microplate are used as controls (lacking the test compound). The mean and standard deviation are determined using the values obtained with these wells (minus the cerulenin controls).

Biochemical Assay of Inhibition of Fatty Acid Biosynthesis: If desired, test compounds identified as antibacterial agents in the above-described assays can be further tested for their ability to inhibit fatty acid biosynthesis in a biochemical assay. For example, compounds identified in the above-described assay can be further tested for their ability to inhibit the enzymes encoded by fatty acid biosynthesis genes, such as fabD, fabH, fabG, fabA, fabI, fabF/B, yjaX, yhfB, ywpB, yjbW, or yjaY. The reactions catalyzed by each of these gene products are set forth above in Table 1, and methods for assaying these reactions are known in the art.

OTHER EMBODIMENTS

It is to be understood that, while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of preparing an inhibitor of bacterial fatty acid biosynthesis (FAB), the method comprising:
   screening multiple test compounds by a method comprising:
      (i) contacting a bacterial cell with a test compound, wherein the bacterial cell contains
         (a) a promoter, the activity of which is increased in the presence of a compound that inhibits FAB, operably linked to
         (b) a reporter gene; and
      (ii) measuring activity of the promoter; and
   identifying candidate compounds that upregulate promoter activity;
   isolating one or more lead compounds from the candidate compounds;
   identifying and selecting a lead compound that inhibits bacterial FAB; and
   formulating the selected lead compound as an inhibitor of bacterial FAB.

2. The method of claim 1, wherein the promoter is PhyfB.
3. The method of claim 1, wherein the promoter is PylpC.
4. A method of preparing an antibacterial agent, the method comprising:
   screening multiple test compounds by a method comprising:
      (i) contacting a bacterial cell with a test compound, wherein the bacterial cell contains
         (a) a promoter, the activity of which is increased in the presence of a compound that inhibits fatty acid biosynthesis (FAB), operably linked to
         (b) a reporter gene;
      (ii) measuring activity of the promoter; and
   identifying candidate compounds that upregulate promoter activity;
   isolating one or more lead compounds from the candidate compounds;
   identifying and selecting a lead compound that inhibits growth of a bacterium; and
   formulating the selected lead compound as an antibacterial agent.

5. The method of claim 4, wherein the promoter is PhyfB.
6. The method of claim 4, wherein the promoter is PylpC.
7. A method for preparing an inhibitor of bacterial fatty acid biosynthesis (FAB), the method comprising:
   screening multiple test compounds by a method comprising:
      (i) contacting a bacterial cell with a test compound, wherein the bacterial cell contains
         (a) a promoter, the activity of which is increased in the presence of a compound that inhibits FAB, operably linked to
         (b) a reporter gene; and
      (ii) measuring activity of the promoter; and
   identifying candidate compounds that upregulate promoter activity;
   isolating one or more lead compounds from the candidate compounds;
   derivatizing said lead compound(s), thereby producing derivatives of said lead compound;
   identifying one or more derivatives that inhibit bacterial FAB; and
   formulating one or more derivatives as inhibitors of bacterial FAB.

8. The method of claim 7, wherein the promoter is PhyfB.
9. The method of claim 7, wherein the promoter is PylpC.
10. A method for preparing an antibacterial agent, the method comprising:
    screening multiple test compounds by a method comprising:
       (i) contacting a bacterial cell with a test compound, wherein the bacterial cell contains
          (a) a promoter, the activity of which is increased in the presence of a compound that inhibits fatty acid biosynthesis (FAB), operably linked to
          (b) a reporter gene;
       (ii) measuring activity of the promoter; and
    identifying candidate compounds that upregulate promoter activity;
    isolating one or more lead compounds from the candidate compounds;

derivatizing said lead compound(s), thereby producing derivatives of said lead compound;

identifying one or more derivatives that inhibit growth of a bacterium; and formulating one or more derivatives as an antibacterial agent.

11. The method of claim 10, wherein the promoter is PhyfB.

12. The method of claim 10, wherein the promoter is PylpC.

13. A method of preparing an inhibitor of bacterial virulence, the method comprising:

screening multiple test compounds by a method comprising:
(i) contacting a bacterial cell with a test compound, wherein the bacterial cell contains
   (a) a promoter, the activity of which is increased in the presence of a compound that inhibits FAB, operably linked to
   (b) a reporter gene;
(ii) measuring activity of the promoter, wherein an increase in activity, relative to the level of activity of the promoter in the absence of the test compound, indicates that the test compound is an inhibitor of bacterial FAB; and
(iii) determining whether the inhibitor of FAB inhibits acylated homoserine lactone synthesis; and identifying candidate compounds that inhibit acylated homoserine lactone synthesis;

isolating one or more lead compounds from the candidate compounds;

identifying and selecting a lead compound that inhibits bacterial virulence; and formulating the selected lead compound as an inhibitor of bacterial virulence.

14. The method of claim 13, wherein the promoter is PhyfB.

15. The method of claim 13, wherein the promoter is PylpC.

16. A method for preparing an inhibitor of bacterial virulence, the method comprising:

screening multiple test compounds by a method comprising:
(i) contacting a bacterial cell with a test compound, wherein the bacterial cell contains
   (a) a promoter, the activity of which is increased in the presence of a compound that inhibits FAB, operably linked to
   (b) a reporter gene;
(ii) measuring activity of the promoter, wherein an increase in activity, relative to the level of activity of the promoter in the absence of the test compound, indicates that the test compound is an inhibitor of bacterial FAB; and
(iii) determining whether the inhibitor of FAB inhibits acylated homoserine lactone synthesis; and identifying candidate compounds that inhibit acylated homoserine lactone synthesis;

isolating one or more lead compounds from the candidate compounds;

derivatizing said lead compound(s), thereby producing derivatives of said lead compound;

identifying one or more derivatives that inhibit bacterial virulence; and formulating one or more derivatives as an inhibitor of bacterial virulence.

17. The method of claim 16, wherein the promoter is PhyfB.

18. The method of claim 16, wherein the promoter is PylpC.

* * * * *

SEQUENCE LISTING

```
<160> NUMBER OF SEQ ID NOS: 12

<210> SEQ ID NO 1
<211> LENGTH: 325
<212> TYPE: DNA
<213> ORGANISM: Bacillus subtilis

<400> SEQUENCE: 1
ttttcttttt catagattcc tatctacact tctctttttt tgtaaaaaac cttcttttta      60
gtaccagata ctaatatcta gtgttataat ctgaccataa ggagtgattc atatgtcaaa     120
agcaaaaatt acagctatcg gcacctatgc gccgagcaga cgtttaacca atgcagattt     180
agaaaagatc gttgatacct ctgatgaatg gatcgttcag cgcacaggaa tgagagaacg     240
ccggattgcg gatgaacatc aatttacctc tgatttatgc atagaagcgg tgaagaatct     300
caagagccgt tataaaggaa cgctt                                           325
```

<210> SEQ ID NO 2
<211> LENGTH: 561
<212> TYPE: DNA
<213> ORGANISM: Bacillus subtilis

<400> SEQUENCE: 2

| | | | | | |
|---|---|---|---|---|---|
| cacatccaac | tgcatacgcc | tcctttccat | ataccatact | ctatgagtaa | gatgaactga | 60 |
| tagtttagac | gaatatattg | ccatgtgaaa | aaaatagga | tagaattagt | acctgatact | 120 |
| aataattgat | cacaacctga | ttgatcttct | aaatttaaga | tataaaggag | tcttccctaa | 180 |
| tgaaagctgg | aatacttggt | gttggacgtt | acattcctga | gaaggtttta | acaaatcatg | 240 |
| atcttgaaaa | aatggttgaa | acttctgacg | agtggattcg | tacaagaaca | ggaatagaag | 300 |
| aaagaagaat | cgcagcagat | gatgtgtttt | catcacatat | ggctgttgca | gcagcgaaaa | 360 |
| atgcgctgga | acaagctgaa | gtggctgctg | aggatctgga | tatgatcttg | gttgcaactg | 420 |
| ttacacctga | tcagtcattc | cctacggtct | cttgtatgat | tcaagaacaa | ctcggcgcga | 480 |
| agaaagcgtg | tgctatggat | atcagcgcgg | cttgtgcggg | cttcatgtac | ggggttgtaa | 540 |
| ccggtaaaca | atttattgaa | t | | | | 561 |

<210> SEQ ID NO 3
<211> LENGTH: 388
<212> TYPE: DNA
<213> ORGANISM: Bacillus subtilis

<400> SEQUENCE: 3

| | | | | | |
|---|---|---|---|---|---|
| tgtgttaaga | gatgaattgc | tgaagagcgg | agtaatggac | ggggaaaaat | taagctgagt | 60 |
| atcagaagtt | tttggtgttc | agccagaaac | aatcgttgca | ttccaatcta | tgaaattata | 120 |
| tactactatt | agtacctagt | cttaattgtc | cggatggtgt | ttagatatga | aagaaataa | 180 |
| gagagaacgc | caggaattac | ttcagcagac | gattcaagca | ccccctttta | ttacagatga | 240 |
| agaactagcg | ggtaaattcg | gggtgagcat | ccagacgata | cgtttggacc | gcttagagct | 300 |
| ttccataact | gaactgagag | aaagaattaa | gaacgtggca | gagaaaacac | ttgaggacga | 360 |
| agtgaagtcc | ctgtcacttg | atgaagtt | | | | 388 |

<210> SEQ ID NO 4
<211> LENGTH: 470
<212> TYPE: DNA
<213> ORGANISM: Bacillus subtilis

<400> SEQUENCE: 4

| | | | | | |
|---|---|---|---|---|---|
| ctagtctcgt | ataatctctc | actttccccg | acatttcacc | caccccttcg | ttttggttac | 60 |
| gctttcatta | taattgtaac | ggtataattt | atcaattccg | aaacaaaata | tttacgcact | 120 |
| aactatcatt | gtaagcggtt | tatgctataa | ttttgacaag | tgaaactaaa | cgaataaatg | 180 |
| aggaatgcgt | atgttaaaat | accagcaaat | cgcaacggaa | attgaaacat | atatagaaga | 240 |
| acaccagctt | cagcagggag | acaaactgcc | agtcctagaa | accctcatgg | cccagtttga | 300 |
| agtcagcaaa | agcaccatca | caaagtccct | cgagctatta | gagcaaaaag | gcgcgatctt | 360 |
| tcaggtcaga | ggaagcggca | ttttcgtcag | aaaacataaa | cgaaaggct | atatcagcct | 420 |
| tctgtcgaat | cagggattta | aaaaagatct | cgaggatttc | aacgtcacct | | 470 |

```
<210> SEQ ID NO 5
<211> LENGTH: 28
<212> TYPE: DNA
<213> ORGANISM: Artificial Sequence
<220> FEATURE:
<223> OTHER INFORMATION: Primer

<400> SEQUENCE: 5
ttttcttttt catagattcc tatctaca                                        28

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
aagcgttcct ttataacggc                                                 20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
cacatccaac tgcatacgcc                                                 20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
attcaataaa ttgtttaccg                                                 20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
tgtgttaaga gatgaattgc                                                 20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
aacttcatca agtgacaggg                                                 20
```

```
<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
ctagtctcgt ataatctctc                                                   20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
aggtgacgtt caaatcctcg                                                   20
```